United States Patent [19]

Toda

[11] Patent Number: 4,976,834

[45] Date of Patent: Dec. 11, 1990

[54] ASYMMETRIC PHOTOCHEMICAL REACTION PROCESS

[75] Inventor: Fumio Toda, Ehime, Japan

[73] Assignee: Daicel Chemical Industries, Ltd., Sakai, Japan

[21] Appl. No.: 173,994

[22] Filed: Mar. 28, 1988

[30] Foreign Application Priority Data

Apr. 3, 1987 [JP] Japan .................................. 62-82256

[51] Int. Cl.$^5$ ............................................. B01J 19/08
[52] U.S. Cl. ........................ 204/157.69; 204/157.71; 204/157.82; 204/157.72; 204/157.87; 204/157.93
[58] Field of Search ...................... 204/157.69, 157.71, 204/157.82, 157.87, 157.88, 157.89, 157.92, 157.93, 157.98, 157.99, 157.72

[56] References Cited

U.S. PATENT DOCUMENTS

| | | | |
|---|---|---|---|
| 3,507,761 | 4/1970 | Kropp | 204/157.93 |
| 3,576,008 | 4/1971 | Schumacher | 204/157.69 |
| 4,754,029 | 6/1988 | Kaneko | 204/157.71 |
| 4,898,654 | 2/1990 | Toda | 204/157.71 |

OTHER PUBLICATIONS

M. E. Kuehne, D. A. Horne, "Photochemical Cyclization of Olefinic N–Chloroamides", J. Org. Chem., vol. 40, No. 9, 1975, pp. 1287–1292.

*Primary Examiner*—John F. Niebling
*Assistant Examiner*—Ben C. Hsing
*Attorney, Agent, or Firm*—Flynn, Thiel, Boutell & Tanis

[57] ABSTRACT

An optically active substance having an optical purity of at least 50% e.e. is obtained by an asymmetric photochemical reaction by converting a starting, achiral material in a chiral crystalline form and irradiating light to the chiral crystalline form to effect the photocyclization of the starting material.

11 Claims, No Drawings

ASYMMETRIC PHOTOCHEMICAL REACTION PROCESS

This invention relates to an asymmetric photochemical reaction process whereby an optically active compound of a high optical purity is obtained through a synthesis via photochemical conversion.

Recently, optically active substances have been becoming more and more valuable as, for example, drugs, agrochemicals, perfumes, liquid crystals or intermediates therefor. However, it is generally very difficult to obtain these optically active substances. Although there have been developed a number of methods for asymmetric synthesis or optical resolution, they can only be applied to a very limited number of compounds. Furthermore, these methods frequently give only limited optical purities. Therefore, it has been urgently required to establish a novel process for preparing an optically active compound.

Photochemical reactions, whose pathways are completely different from those of usual chemical reactions, have been employed for synthesizing various products.

It has been frequently attempted to prepare an optically active substance through a photochemical reaction. However, there has scarcely been reported any outstanding success in the photosynthesis of an optically active substance from an achiral compound.

For example, there has been known a process wherein a β-lactam is prepared by the photocyclization of an α-keto acid amide by utilizing an asymmetric field formed by deoxycholic acid as shown hereinbelow (Chem. Commun., 333 (1983)), but the optically active substance thus obtained shows only a limited optical purity, i.e., 15 % e.e.

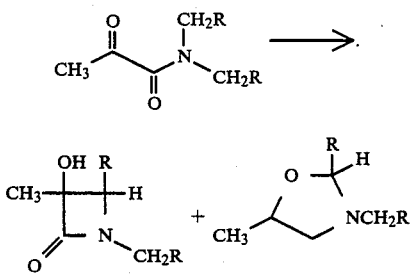

In the above shown chemical reaction, R is hydrogen or an alkyl.

The present inventors have found that when an achiral starting material is irradiated with light in the chiral crystalline form during an intramolecular photocyclization, said starting material is affected by the chiral field of the crystalline structure and consequently forms an optically active product with a high enantiomer selectivity, thus completing the present invention.

SUMMARY OF THE INVENTION

Accordingly the present invention relates to an asymmetric photochemical reaction process wherein an achiral starting material is converted into another material by photocyclization or chemical conversion, proceeding via the same, characterized in that said starting material is irradiated with light in the chiral crystalline form to thereby give an optically active substance having an optical purity of at least 50 % e.e.

The invention provides a process for obtaining an optically active substance, having an optical purity of at least 50% e.e., by the asymmetric photochemical reaction, which comprises the steps of preparing a starting, achiral material in a chiral crystalline form and irradiating light to the chiral crystalline form to effect the photocyclization of the starting material.

The process of the invention may comprise a further step of isolating the optically active substance. The isolation step may be conducted with further chemical conversion of the product(s) obtained in the photocyclization step.

The process of the invention includes two embodiments. In one embodiment, the chiral crystalline form is prepared by crystallizing the starting material and an optically active compound in combination. The crystallization is conducted with a solution in a solvent or solvents of the starting material and the optically active compound. The optically active compound preferably includes a compound having the below defined formula (I) and in particular 1,1'-binaphthol, 9,9'-biphenanthrol, α-, β-or γ-cyclodextrin, cholic acid, deoxycholic acid or brucine.

In the other embodiment, the chiral crystalline form is prepared from the starting, achiral material, without the use of any optically active compound, to obtain enantiomorphically pure crystals which will be able to be converted to an optically active cyclized product(s) by way of the light irradiation. It is preferred that the enantiomorphically pure crystals are formed by seeding them with a small amount of another enantiomorphically pure crystals. The preferable starting achiral material includes an alkylamide of α-ketocarboxylic acid and the resulting product is a β-lactam.

In addition, the process of the invention may comprise a further step of grinding the resulting crystals into powder before the light irradiation step. The isolation may be advantageously conducted with chromatography.

In the present invention, the achiral starting material may be subjected to any intramolecular photocyclization. Examples of the reaction type include the following ones:

(Reaction type)

optical ring closure:

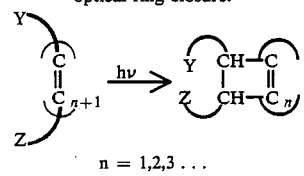

n = 1,2,3 . . .

intramolecular photocycloaddition:

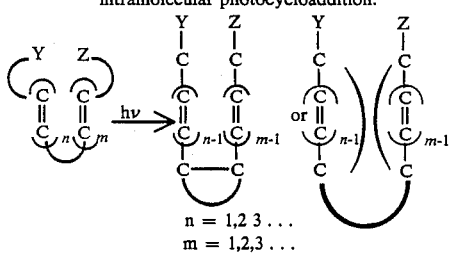

n = 1,2 3 . . .
m = 1,2,3 . . .

Norrish type II cyclization:

-continued

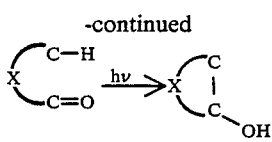

wherein Y and Z may be each any atomic group; alternately they may be in the same atomic group forming a cyclic structure, though it is preferable that either one or both of them include hetero atom(s); and X represents an atomic group having two carbon atoms as the main chain, either one of which may be a hetero atom, optionally carrying any substituent(s) thereon.

The term "chemical conversion proceeding via photocyclization" means the whole process including the secondary change(s) of the product obtained by the above reaction which may occur during the subsequent isolation and purification steps. For example, a compound 4which will be described in the following Example is thought to be formed by the secondary decomposition of a compound 3 which is obtained by photocyclization of a compound 2, during the isolation and purification steps.

The term "chiral crystal" as used herein means one lacking plane symmetry in the crystalline lattice or in the molecular structure forming the same. It is self-evident that a crystal incorporating an optically active molecule therein as a component other than the starting material, i.e., a clathrate crystal, which will be described hereinbelow, is chiral, there being no need to resort to the analysis of its structure. For example, it is known that various compounds carrying a carbonyl group or an ether bond would form a crystal together with an optically active compound 1 as shown by the following formula (I):

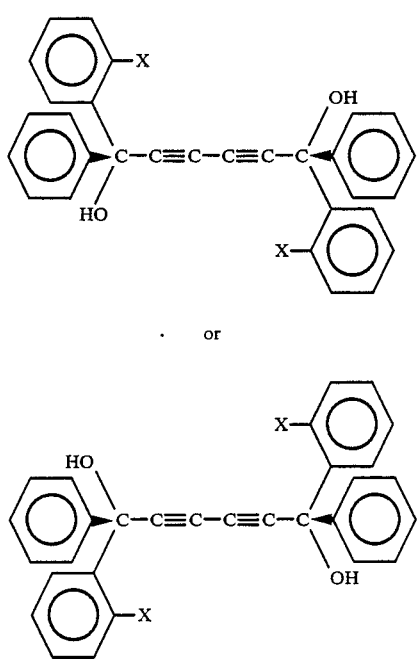

wherein X represents Cl, Br, I or F or an alkyl group having up to four carbon atoms.

Such a chiral crystal may be obtained through crystallization from a solution of a mixture of the compound 1 with an achiral starting material.

Any achiral starting material may be used therefor, so long as it can be photocyclized under irradiation with light to thereby give the aimed optically active substance. In order to effect the reaction at a high optical yield in the presence of the optically active compound 1 however, it is preferable that the following requirements be satisfied: (1) the compound 1 can transmit the exciting light for the starting compound to a certain extent; (2) the compound 1 would not inactivate the excited state of the starting material; and (3) the compound 1 incorporates the starting material therein to thereby form a crystalline clathrate compound.

When the abovementioned process is to be carried out in practice, it is preferable to dissolve the compound 1 of the above formula (I) together with the starting material in a common solvent followed by isolation of the resulting clathrate complex as crystals. Then the crystals thus obtained are irradiated with light of a wavelength suitable for photochemical conversion. In the irradiation, it is preferable that the crystals are appropriately ground and then spread to thereby enlarge the exposure area, since the irradiation efficiency can be improved thereby. Although the product may be separated from the compound 1 in any conventional manner such as distillation, extraction or substitution with a guest compound having a higher affinity, the separation can be readily effected by chromatographing the reaction mixture as such.

On the other hand, a chiral crystal having no optically active molecule is sometimes observed. In this case, the chirality of said crystal can be proved when the crystalline form can be clearly observed or the crystal can be subjected to X-ray diffractometry. It is sometimes difficult, however, to carry out these analyses When crystals obtained from an achiral starting material forms an optically active substance, the result obviously suggests that said crystals have a chiral structure. In order to selectively obtain these crystals, recrystallization may be carried out from a solution thereof by using an optionally ground crystal of the starting material as a crystal seed. On the other hand, the irradiation with light may be carried out in the same manner as the one applied to a clathrate crystal having an optically active molecule. This process is never accompanied by any trouble such as light-absorption or inactivation by an optically active molecule added as an aid.

Any conventional photochemical reaction can scarcely achieve such a high asymmetry yield as the one observed by the process of the present invention. According to the process of the present invention, an asymmetry yield amounting to 50 % e.e. to 100 % e.e. can be realized. This effect is caused by the fact that the reaction of the present invention proceeds in a chiral field of the crystalline structure and thus suffers from an intense steric hindrance thereby; or that the starting material have a fixed optically active conformation in the crystalline structure. Thus a high optical yield can be achieved in the crystalline lattice.

According to the process of the present invention, cyclopentenones 4a and 4b can be obtained from tropolone ethers 2a and 2b with an optical purity of 70 % e.e. or above, as will be shown in the Examples hereinafter. These products are intermediates for prostaglandins which have recently attracted attention as a medicine. Further the compounds 6, 8, 9 and 11 as will be shown in the Examples hereinafter have each a basic skeleton of β-lactam antibiotics. Therefore they are available in synthesizing these antibiotics through similar reactions. Thus it is expected that the process of the present invention considerably contributes to the supply of optically active substances which are highly useful.

EXAMPLES

To further illustrate the present invention, and not by way of limitation, the following Examples for preparing an optically active substance with a high optical purity (or e.e.) will be given.

EXAMPLE 1

9.66 g of a starting material 2a (R=CH$_3$) as shown in Table 1 and 2.76 g of a compound (R)—(—)—1 (X=Cl) of the general formula (I) were dissolved in 50 ml of a benzene/n-hexane mixture (1 : 1). The resulting solution was allowed to stand at room temperature for 12 hours. Thus a clathrate complex in the form of colorless needles was formed (yield: 10.40 g, m.p.: 69°–71° C.). This clathrate complex was irradiated with a high-pressure mercury lamp for 72 hours while grinding the same in an agate mortar every six hours. The obtained product was isolated by column chromatography wherein silica gel and chloroform were used as a stationary phase and as a mobile phase, respectively. The optical purity (% e.e.) of the isolated product was determined from the angle of rotation thereof. Table 1 shows the results.

EXAMPLE 2

A clathrate compound was obtained from a starting material 2b (R=C$_2$H$_5$) and a compound (R)—(—)—1 (X=Cl) of the general formula (I) by the same method as the one described in Example 1 (m.p.: 135°–137° C.). After irradiation with UV light for 83 hours, the product was isolated. Table 1 shows the results.

TABLE 1
Starting materials and products of Examples 1 & 2

| | Starting material | Product | [α]$_D$ (MeOH, 0.2 M) | Yield* | Optical purity (% e.e.) |
|---|---|---|---|---|---|
| Ex. 1 | 2a | 3a | −168° | 11% | 100% |
| | | 4a | +89.5° | 26% | 91% |
| Ex. 2 | 2b | 3b | −189° | 12% | 100% |
| | | 4b | +59.3° | 14% | 72% |

Note: Determined when about a half of the starting material reacted. Compound 4 may be a secondary product from compound 3.
*Calculated based on the consumed starting material.

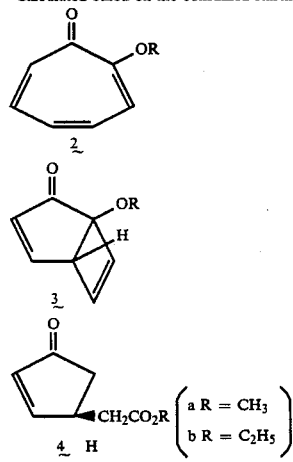

EXAMPLE 3

A clathrate complex obtained from the following compound 5 and the same compound (R)—(—)—1 of the general formula (1) as the one used in Example 1 was crystallized from a mixture of ether/petroleum ether (1:1 by volume) to give prisms. This complex was irradiated with a high-pressure mercury lamp (400 W) for 27 hours while grinding the same in an agate mortar every one hour.

After the completion of the reaction, the product was isolated by column chromatography. Thus a compound 6 of the following formula was obtained at a yield of 82.6 %. It was proved to be completely optically pure, i.e., 100 % e.e., by analyzing the same by using an optical resolution column CHIRACEL OC in hexane/IPA (9:1). The (—)—6 thus formed was in the form of plate prisms (m.p.: 123°–124° C.,[α]$_D$−99.7 in CHCl$_3$, 0.34 M).

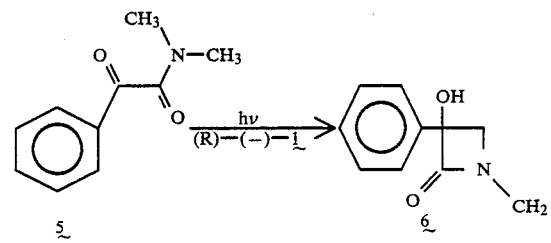

EXAMPLE 4

A complex was formed from a compound 7a as shown in Table 2 and a compound (R)—(—)—1 by the same method as the one described in Example 1 and irradiated with light for 100 hours. The resulting β-lactams 8a and 8b as shown in Table 2 had optical purities of 62.5 % e.e. and 95 % e.e., respectively, each determined by using an optical resolution column CHIRACEL OC.

EXAMPLE 5

A complex was formed from a compound 7b as shown in Table 2 and the compound 1 by the same method as the one described in Example 4 and irradiated with light for 50 hours. The optical purity of the β-lactam 8b thus obtained as determined by using CHIRACEL OC was 55.8%.

TABLE 2

Starting materials and products of Examples 4 & 5

| | Starting material 7 | | Product 8 % e.e. | [α_D] | 9 % e.e. | [α_D] | Ratio (8:9) | Yield (8 + 9) |
|---|---|---|---|---|---|---|---|---|
| Ex. 4 | 7a | X=CH₂ | 8a 62.5 | −62.4° | 9a 95 | −62.4° | 57:43 | 67% |
| Ex. 5 | 7b | X=O | 8b 55.8 | −107.8° | 9b unknown | −48.7° | 78:22 | 49% |

Note: [α_D] was determined in CHCl₃ at 1 M.

EXAMPLE 6

A compound 10 was crystallized from benzene and a piece of the crystal thus formed was ground. By using the ground crystal piece as a crystal seed, crystals of the compound 10 were obtained from a benzene solution thereof. The obtained crystals were ground in an agate mortar and 0.10 g thereof was irradiated with a high-pressure mercury lamp (400 W) at room temperature. A small amount of the compound 10 remained even after continuing the irradiation for 40 hours. Then the product was isolated by column chromatography wherein a benzene/chloroform mixture was used as an eluent while silica gel was used as a stationary phase. Thus 0.76 g (74%) of the main product 11 was obtained. The angle of rotation of this product was $[\alpha]_D + 116.4$ (0.5 M, CHCl₃) while the optical purity thereof determined by using CHIRALCEL OC was 90 % e.e.

EXAMPLE 7

Crystals were obtained in the same way as shown in Example 6 except for using pieces of the ground crystals antipodal to those used in Example 6 as a crystal seed. 0.113 9 of the resulting crystals were 9round and irradiated with light as in Example 6. The obtained product was isolated by chromatography (yield: 70 %). The angle of rotation of the compound 11 thus obtained was $[\alpha]_D - 96.3$ (0.5 M, CHCl₃).

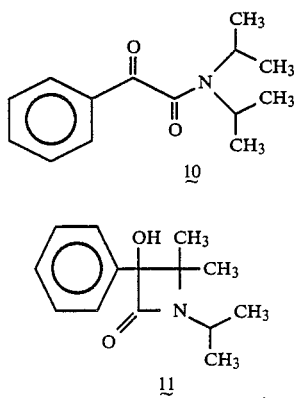

What is claimed is:

1. A process for obtaining an optically active substance having an optical purity of at least 50% e.e. by an asymmetric photochemical reaction, comprising the steps of: (1) mixing an achiral first compound with a second compound in a solvent to form chiral clathrate crystals of said first and second compounds; (2) irradiating the crystals to effect the photocyclization of said first compound; and (3) isolating the optically active substance.

2. A process as claimed in claim 1, in which the isolation step is conducted with further chemical conversion of the product(s) obtained in the photocyclization step.

3. A process as claimed in claim 1, in which the chiral crystals are prepared by crystallization the achiral first compound and said second compound, which is optically active, in combination.

4. A process as claimed in claim 3, in which the optically active second compound has the formula (I):

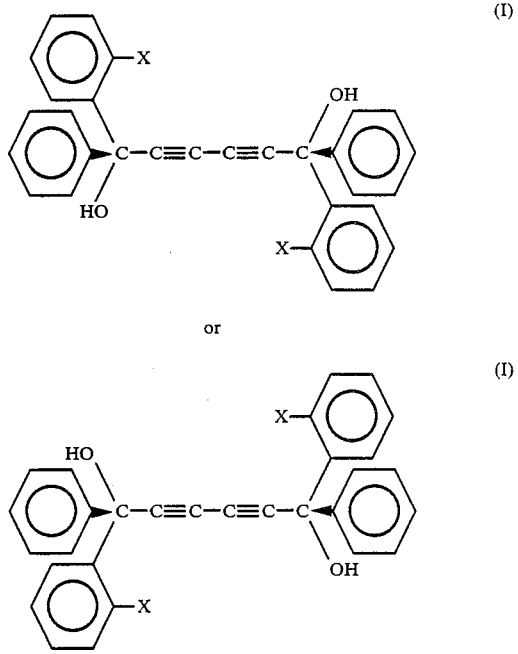

5. A process, as claimed in claim 3, in which the optically active second compound is selected from the group consisting of 1,1'-binaphthol, 9,9'-biphenanthrol, α-, β- or γ-cyclodextrin, cholic acid, deoxycholic acid and brucine.

6. A process as claimed in claim 1, n which the chiral crystals are prepared from the achiral first compound, without the use of any optically active compound, to obtain enantiomorphically pure crystals which will be able to be converted to an optically active cyclized product(s) by way of the irradiation.

7. A process as claimed in claim 6, in which the enantiomorphically pure crystals are formed by seeding them with a small amount of other enantiomorphically pure crystals.

8. A process as claimed in claim 6, in which the achiral first compound is an alkyamide of α-ketocarboxylic acid and the product is a β-lactam.

9. A process as claimed in claim 1, which comprises the further step of grinding the crystals into powder before the light irradiation step.

10. A process as claimed in claim 1, in which the isolation step is conducted with chromatography.

11. A process for obtaining an optically active substance having an optical purity of at least 50% e.e. by an asymmetric photochemical reaction, comprising the steps of: (1) mixing an achiral first compound with a second compound in a solvent to form chiral clathrate crystals of said first and second compounds; and (2) irradiating the crystals to effect the photocyclization of said first compound.

* * * * *

UNITED STATES PATENT AND TRADEMARK OFFICE
CERTIFICATE OF CORRECTION

PATENT NO. : 4,976,834
DATED : December 11, 1990
INVENTOR(S) : Fumio TODA

It is certified that error appears in the above-identified patent and that said Letters Patent is hereby corrected as shown below:

On title page, at item [73], change to read as follows:
  ---Daicel Chemical Industries, Ltd., Sakai-shi,
     Osaka, Japan---.

Column 8, line 30; change "crystallization" to
  ---crystallizing---.
        line 62; after "process" delete the comma.
        line 67; change "n" to ---in---.
Column 9, line 12; change "alkyamide" to ---alkylamide---.

Signed and Sealed this

Twenty-eighth Day of July, 1992

*Attest:*

DOUGLAS B. COMER

*Attesting Officer*      *Acting Commissioner of Patents and Trademarks*